United States Patent [19]
Phillips et al.

[11] 4,428,905
[45] Jan. 31, 1984

[54] SYSTEM FOR THE PRODUCTION OF KETENE AND METHYLENE FROM LIMESTONE UTILIZING A SOLID ELECTROLYTE ELECTROLYSIS CELL

[75] Inventors: D. Colin Phillips, Monroeville; Werner S. Emmerich, Churchill Borough; Arnold O. Isenberg, Forest Hills; Michael G. Down, Plum Borough, all of Pa.

[73] Assignee: Westinghouse Electric Corp., Pittsburgh, Pa.

[21] Appl. No.: 266,672

[22] Filed: May 22, 1981

[51] Int. Cl.³ .............................................. G21C 15/00
[52] U.S. Cl. .................................... 376/323; 568/301; 568/383
[58] Field of Search ................. 376/323, 324; 568/301, 568/302, 383, 411, 467

[56] References Cited

U.S. PATENT DOCUMENTS

| | | | |
|---|---|---|---|
| 3,181,999 | 5/1965 | Schulten | 376/323 |
| 3,228,850 | 1/1966 | Fellows | 376/233 |
| 3,402,230 | 9/1968 | White, Jr. | 264/104 |
| 3,558,724 | 1/1971 | Salotti | 260/676 |
| 4,021,298 | 5/1977 | Jones | 376/324 |
| 4,158,637 | 6/1979 | Jones | 376/324 |

OTHER PUBLICATIONS

Acetylene Homologs and Derivatives, P. Pigniol, New York, (1950) pp. 155–169.
Organic Chemistry, Morrison and Boyd, Boston, 1966, Section 4.33.
College Chemistry, 9 Ed., Barnes S. Noble, N.Y. (1971) p. 258–261.

*Primary Examiner*—Sal Cangialosi
*Attorney, Agent, or Firm*—D. P. Cillo

[57] ABSTRACT

Organic hydrocarbon materials are produced from plentiful inorganic limestone type materials by: (1) thermally decomposing the limestone type materials to produce CaO and $CO_2$, (2) using the $CO_2$ in a solid electrolyte electrolysis cell to produce CO, (3) catalytically decomposing the CO to produce carbon, (4) reacting the carbon with the CaO produced in step (1), to produce $CaC_2$, (5) hydrolyzing the $CaC_2$ toi produce $C_2H_2$, (6) catalytically reacting the $C_2H_2$ with steam to produce $CH_3COCH_3$, (7) pyrolyzing the $CH_3COCH_3$ to provide ketene and methane, and separating the ketene. The ketene may then be decomposed to provide methylene, which can be reacted with an alkane, such as methane in an insertion chain reaction, to provide organic hydrocarbon materials. An in-place nuclear reactor can provide energy for the endothermic reactions of the system.

16 Claims, 3 Drawing Figures

SYSTEM FOR THE PRODUCTION OF KETENE AND METHYLENE FROM LIMESTONE UTILIZING A SOLID ELECTROLYTE ELECTROLYSIS CELL

BACKGROUND OF THE INVENTION

Coal can be efficiently converted into hydrocarbons of a more useful gaseous or liquid form by coal gasification or liquefaction techniques, utilizing energy from a high-temperature, gas-cooled nuclear reactor for the endothermic and/or electrolytic processing required, as taught by Jones, in U.S. Pat. No. 4,158,673. While the United States, the Soviet Union, and China still contain major deposits of coal, this mineral is considered precious in most other parts of the world, where deposits are either lacking or have been largely used up.

Thus, while the earth's supply of precious fossil fuels is being steadily depleted to provide electricity and petrochemicals, a virtually unlimited world-wide supply of other carbon bearing minerals remains untapped as an energy source. Salotti, in U.S. Pat. No. 3,558,724, taught that inorganic crystalline carbonates could provide gaseous products containing up to 4% methane, if the carbonates were first heated in an oxygen-free atmosphere at from about 400° C. to 700° C., and then contacted with excess hydrogen gas at from about 200 psi. to 10,000 psi. This process, however, uses large quantities of valuable hydrogen gas, which is becoming increasingly important itself as an energy source. In addition, this process provides a poor yield of methane, leaves carbon residue and maintains explosive reaction conditions.

What is needed is a method to produce high carbon chain hydrocarbons without using valuable fuels such as coal or hydrogen.

SUMMARY OF THE INVENTION

It has been discovered that the above-described need can be met by a process comprising the steps of: (1) thermally decomposing an inorganic, crystalline, carbon-containing mineral material, such as $CaCO_3$, at a temperature of between about 700° C. and about 1,000° C., to produce $CaO$ and $CO_2$, (2) using the $CO_2$ as a feed gas to an electrolysis cell effective to produce $CO$ and $O_2$. Preferably, the electrolysis cell is a high temperature solid electrolyte type, operating above about 800° C., utilizing an electrolyte, such as $Y_2O_3$ doped $ZrO_2$, through which oxygen ions formed at the cathode electrolyte interface can migrate, (3) decomposing the $CO$ exiting the electrolysis cell at a temperature of between about 450° C. and about 550° C. in the presence of a suitable catalyst, such as iron or stainless steel, to produce dry, free-flowing C particles, and $CO_2$ which can be recycled to the electrolysis cell, (4) reacting the C with the calcium oxide formed in the first step, usually in an electric arc furnace at a temperature of between about 1,600° C. and about 2,000° C. to produce $CaC_2$ and $CO$, where the $CO$ can be recycled to make additional carbon, (5) hydrolyzing the $CaC_2$ to provide $C_2H_2$ (acetylene gas) and $Ca(OH)_2$, (6) reacting the $C_2H_2$ with steam at between about 250° C. and about 475° C. in the presence of a catalyst such as $ZnO$, to provide $CH_3COCH_3$ (acetone) and hydrogen gas the $C_2H_2$ does not have to be purified for this reaction to occur, (7) pyrolyzing the $CH_3COCH_3$ at between about 600° C. and about 800° C., to provide ketene gas, which is then cooled to $-60°$ C. by a suitable cooling means, to provide a ketene product ($CH_2\!\!=\!\!C\!\!=\!\!O$) in liquid form, and separable methane gas. The ketene can then be stored as a liquid at 25° C. under a pressure of about 40 psi, if desired.

In hydrolysis step (5), approximately 26,540 kcal of heat is liberated for each mole of $CaC_2$. Some of this heat can be used in other parts of the reaction cycle. The $Ca(OH)_2$ from step (5) can be separated from the carbide for use in other industries, such as an alkali for water treatment, etc. By-product hydrogen from step (6) and methane from step (7) can be separated and used as fuels. The limestone thermal decomposition, fuel cell electrolysis, arc furnace production of calcium carbide, and the pyrolysis step to provide ketene require a large expenditure of energy, which could be supplied by a pressurized, liquid cooled nuclear reactor, or a high-temperature, gas-cooled nuclear reactor, without major modifications in design or structure of the reactor. Energy from the nuclear reactor could also be used to provide steam and heat to produce acetone from acetylene. Thus, uranium would be the chief fuel consumed in the process of converting the inorganic carbon into an organic carbon, which can be used to produce liquid hydrocarbon fuels such as diesel oil or gasoline.

The ketene can be photochemically decomposed or thermally decomposed to produce extremely reactive, organic methylene. A particular type of insertion chain reaction sequence could then be started between methylene and alkanes, such as methane, which could be easily supplied as a by-product from the pyrolysis reaction. This could ultimately result in a mixture of ethane, propane, butane, pentane, hexane, heptane, and possibly higher carbon chain hydrocarbons such as octane. The pyrolysis of acetone, the decomposition of ketene and the methylene insertion chain reaction to form ethane and higher hydrocarbons, can be accomplished as separate steps, or they can be combined in various fashions. Thus, by the method of this invention, limestone type minerals can be reacted to form gasoline-type molecules via a ketene reaction sequence, utilizing energy from an already existing nuclear power source.

BRIEF DESCRIPTION OF THE DRAWING

For a better understanding of the invention, reference may be made to the preferred embodiments, exemplary of the invention, shown in the accompanying drawings, in which.

DESCRIPTION OF THE PREFERRED EMBODIMENTS

Figure 1:
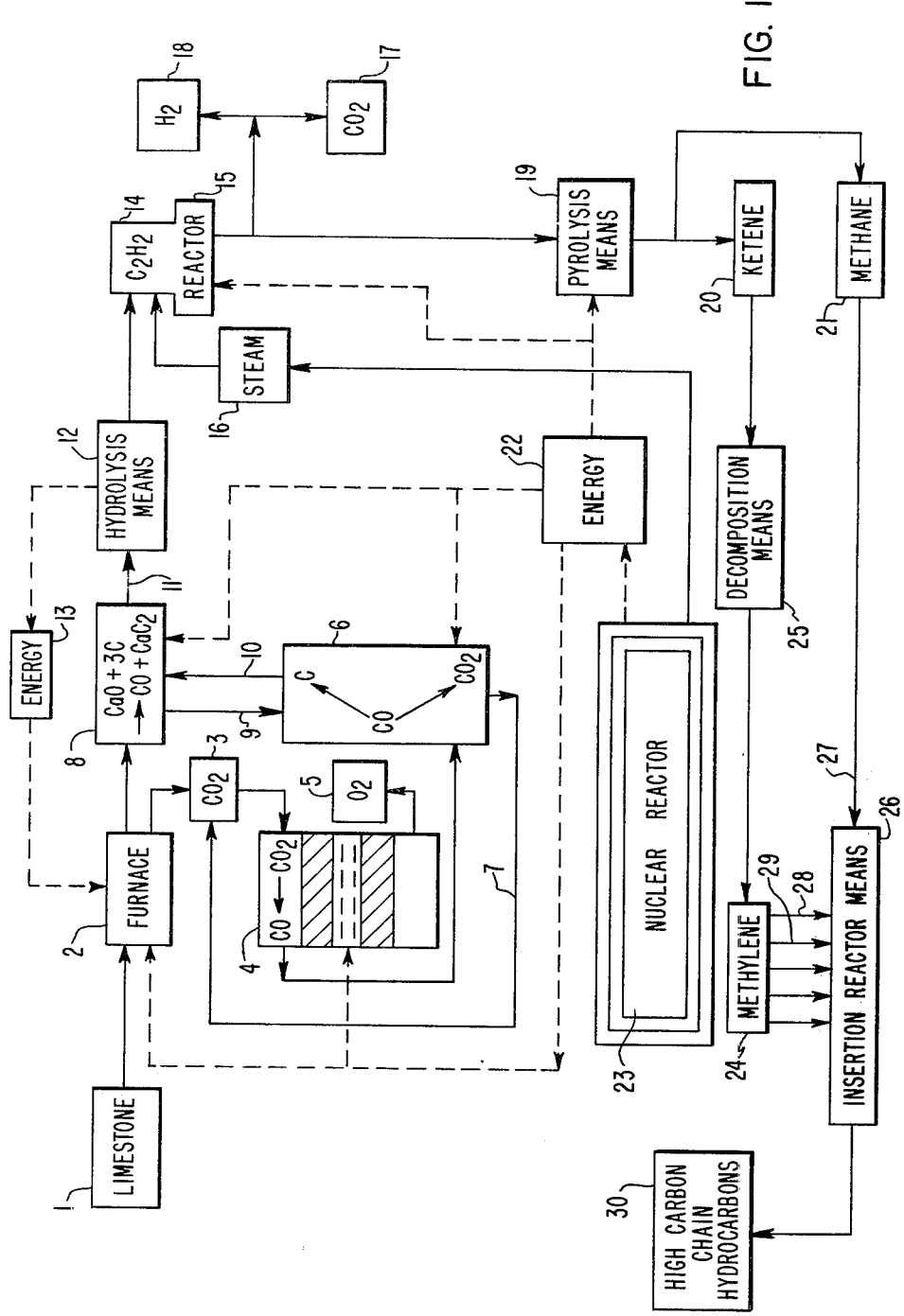
FIG. 1 is a flow chart of one embodiment of the system of this invention.

The starting material 1, for the system of this invention, shown in FIG. 1 of the Drawings, is an inorganic, crystalline or non-crystalline, carbon containing mineral material. These are usually carbonate containing materials, preferably a limestone type ($CaCO_3$). Useful carbonates are selected from: calcite ($CaCO_3$), dolomite ($CaMg(CO_3)_2$), siderite ($FeCO_3$), magnesite ($MgCO_3$), rhodochrosite ($MnCO_3$), smithsonite ($ZnCO_3$), arajonite ($CaCO_3$), witherite ($BaCO_3$), strontianite ($SrCO_3$), cerussite ($PbCO_3$), malachite ($CuCO_3(OH)_2$), azurite ($Cu_3(CO_3)_2(OH)_2$), their mixtures, and the like.

These carbonate materials, alone or in mixtures, are fed into an electric furnace or an electric kiln 2, in the presence of air, at a temperature of between about 700° C. and about 1,000° C., to provide CaO (quicklime) and $CO_2$, according to the following chemical reaction when $CaCO_3$ is the starting material:

$$2CaCO_3 \xrightarrow{900° C. \text{ heat}} 2CaO + 2CO_2 \qquad (1)$$

Temperatures should be kept below about 1,000° C. or the CaO could react with any silicon dioxide impurities present in the limestone feed. While this and subsequent reactions start with $CaCO_3$, other of the above-described feed materials would follow a similar process.

Figure 2:
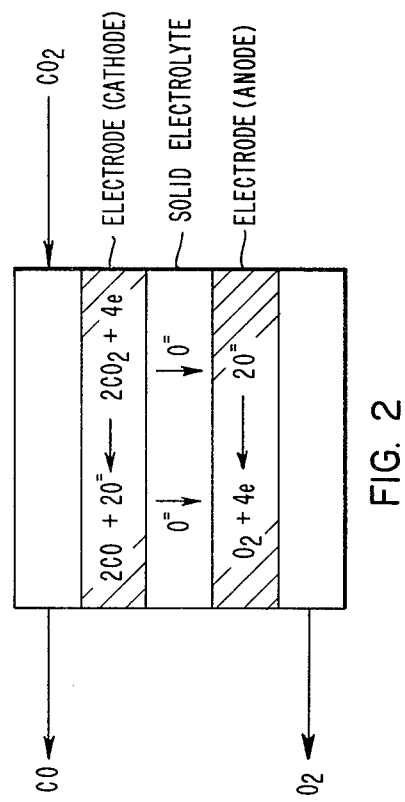
FIG. 2 is a schematic illustration of one embodiment of a suitable electrolysis cell for the method of this invention.

The carbon dioxide 3 is collected and used as a fuel in an electrolysis cell 4 effective to produce CO and oxygen 5. The term "cell" is used herein to mean one or a series of connected cells. Preferably the electrolysis cell is a high temperature solid electrolyte type, operating above about 800° C., utilizing an electrolyte, made from zirconia that is doped with two valent or three valent metals to render an oxygen ion conducting mixed oxide. Here, 5 mole % to 15 mole % of yttria in zirconia is a preferred oxide mixture, for example $(ZrO_2)_{0.9}(Y_2O_3)_{0.1}$, which is effective to allow oxygen ion ($O^=$) transport therethrough, from the cathode to the anode, as shown in FIG. 2 of the drawings.

The electrolysis unit for $CO_2$ conversion can comprise, for example, tubular electrolysis cells preferably of the thin film electrolyte type, that are supported on a mechanically strong porous support. Several cells can be electrically connected on the same support, or single tubular cells can be used with appropriate current collectors. The low resistance thin film electrolyte is contacted by inner and outer electrodes of, for example, Pt or sintered $Pt-ZrO_2$. With Pt electrodes, either electrode can be chosen as the oxygen-producing anode. Other anodes can be made from electronically conducting oxides, such as calcium or strontium doped lanthanum maganite, tin doped indium oxide, calcium or strontium doped lanthanum nickel oxide, or calcium or strontium doped lanthanum cobalt oxide, to name only a few. Cathodes can be made from $Ni-ZrO_2$, $Co-ZrO_2$ and $Fe-ZrO_2$ cermet layers besides noble metals.

The yttrium oxide acts to stabilize the solid electrolyte, preventing volume changes during thermal cycling, and allowing ion transport by virtue of the anion vacancies generated in the zirconia structure upon cationic substitution of yttrium, calcium, or rare earth metals for zirconium. U.S. Pat. No. 3,402,230, to White, can be referred to for a description of the structure of one type of tubular, solid electrolyte cell, as well as details involving useful electrodes and stabilized zirconia electrolyte.

A base plate for the stacked cells can be provided with appropriate current leads, the cells can then be supported at the base by insulation and enclosed by an Inconel housing, containing appropriate gas exit lines at the top. To help prevent carbon deposition on the inner Inconel housing and the CO exit lines, an inner copper plating can be used, since the copper would be relatively non-catalytic. Gas circulation can be provided with an appropriate type of diaphragm pump. The electrolysis cell unit can be heated, for example, by an electric multiple-zone split-tube or other type furnace. Optionally, the $CO_2$ feed can be bubbled through a water saturator. This would improve cell efficiency and generate additional hydrogen and oxygen. The overall electrolysis reaction in the electrolysis battery is as follows:

$$2CO_2 \xrightarrow[\text{(electrolysis)}]{800° C.-1,100° C.} 2CO + (O_2) \qquad (2)$$

The CO exiting the electrolysis cell is then catalytically degraded in a suitable stainless steel or other type decomposition means 6, at a temperature of between about 450° C. and about 550° C. in the presence of a suitable catalyst, such as iron or stainless steel. This reaction provides virtually 100% conversion into dry, free-flowing, lamp black type carbon particles and $CO_2$, according to the following chemical reaction:

$$2CO \xrightarrow{500° C. \text{ catalyst}} C + CO_2 \qquad (3)$$

The carbon deposition reactor 6, can comprise, for example, cylindrical reaction vessel, with a scraper means for removing carbon deposits from the inside walls of the reaction vessel, and a removable carbon collection means. The inner lining of the reaction vessel can be made of catalytic iron or stainless steel. Gas feed lines can be made of aluminum-bronze alloy which would be relatively non-catalytic to CO, and would help prevent clogging of the reactor entrance by carbon deposits. The reaction vessel can be heated by an electric, multiple three-zone furnace where heating elements could be wound directly onto the reactor shell.

The $CO_2$ formed can be recycled by line 7 to the electrolysis cell 4, while the carbon produced is reacted with the product quicklime from the initial limestone decomposition reaction (1), to form calcium carbide according to the following chemical reaction:

$$CaO + 3C \xrightarrow{1,800° C.} CaC_2 + CO \qquad (4)$$

The CO formed can be recycled to decomposition reaction (3). Carbide may be formed using a plasma or a thermoelectric arc furnace 8 at a temperature of between about 1,600° C. and about 2,000° C. The arc furnace will usually have a plurality of consumable carbon electrodes carrying alternating electric current. The quicklime and carbon are used as the charge within a rotating furnace crucible. The liquid carbide forms below the tip of each electrode which drags slowly through the charge, acting as stirrers to provide an homogeneous carbide material which eventually is discharged from the crucible. Referring again to FIG. 1 of the drawings, the CO by-product exits the arc furnace 8 via line 9 to the decomposition reactor 6. The carbon from the decomposition reactor 6 enters the arc furnace 8 via line 10. The calcium carbide exits the arc furnace 8 via line 11 to the hydrolysis means 12.

Calcium carbide is still an inorganic, strongly ionic material, being composed of $C_2^{2-}$ anions and $Ca^{2-}$ cations. The conversion of this material into a purely organic, covalent material can be achieved by the hydrolysis of $CaC_2$, at about 25° C., to provide the following materials:

$$CaC_2 + 2H_2O \rightarrow C_2H_2 + Ca(OH)_2 + 26{,}540 \text{ kcal} \qquad (5)$$

The heat energy 13 from this reaction could be used in other parts of the reaction cycle. The hydrolysis reaction temperatures must be controlled by removal of heat, otherwise the acetylene could polymerize or decompose. The calcium hydroxide is recovered for use in other industries, such as an alkali for water treatment, etc.

After the acetylene producing hydrolysis, the acetylene gas 14, which need not be either dried or purified, is passed through a heated, gas tight, steel reactor tube 15, having steam 16 inlet means and gas outlet means. Here the acetylene gas will undergo ketonization hydrolysis in the presence of a catalyst, such as zinc oxide, zinc vanadate, or their mixtures, at between about 250° C. and 450° C., to form acetone ($CH_3COCH_3$) according to the following chemical reaction:

$$2C_2H_2 + 3H_2O \rightarrow CH_3COCH_3 + CO_2 + 2H_2 \quad (6)$$

The velocity of the gases through the tube should be about 450 to 1,000 liters/hour for tube diameters of about 125 mm. An excess of steam may be used, with yields of 80% to 95% at 450° C. The temperature can be maintained, for example, by use of a molten salt bath. This reaction is further described by P. Piganiol, *Acetylene Homologs And Derivatives*, New York, 1950, pp. 155 to 166.

The gas mixture is cooled to condense acetone liquid, usually at 25° C., and the remaining gases 17 and 18 can be further separated to yield $CO_2$, and $H_2$, which can be used as a fuel. In this ketonization step, the zinc catalyst is essential to the production of acetone, since use of other catalysts will produce a variety of other end products, for example, alumina catalyst will produce cyclic furan

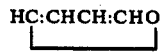

materials, and the deletion of catalyst yields cyclic paraldehyde $C_6H_{12}O_3$. The usual source of acetone is from petroleum where isopropanol can be produced from petroleum hydrocarbon, and can in turn easily be converted to acetone. A combination acetylene ketonation reactor tube-condensation means is shown as 15 in FIG. 1 of the Drawings.

The cooled, liquid acetone is then pyrolyzed at between about 600° C. to about 800° C. in a stainless steel or other suitable furnace, shown as 19 in FIG. 1 of the Drawings. Here, the acetone is decomposed by heat alone without oxidation (pyrolysis), to produce ketene 20 and methane gas 21 according to the following overall chemical reaction:

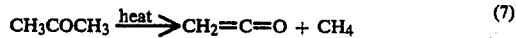

The gas mixture is then cooled to condense ketene liquid, usually at about −60° C. The by-product methane gas, which is separated from ketene, can be used as a fuel, or saved for further processing in the method of this invention. The cooling step here and in the formation of acetone can utilize, for example, a −70° C. bath of acetone and liquid nitrogen surrounding the condensation apparatus. Cooling water associated with a nuclear reactor could also be used. The ketene can be allowed to vaporize for further reactions after separation from methane.

The heat energy 22 required for reactions (1), (2), (3), (4), (6) and (7) can be supplied by an in-place nuclear reactor 23. These endothermic demands can be met by relatively low-cost nuclear energy, derived, for example, from a very high-temperature, gas-cooled, nuclear reactor, or a liquid-cooled nuclear reactor, both well known in the art, and described in detail by Tobin, in U.S. Pat. No. 4,113,563, and Obenmeyer et al., in U.S. Pat. No. 4,173,513, respectively.

In the more common liquid-cooled nuclear reactor, a liquid reactor coolant, such as water, is pumped into the reactor pressure vessel enclosing the nuclear core. The pressurized water circulates around the core where heat energy is absorbed raising its temperature to about 400° C. The hot pressurized water is then passed out of the reactor vessel to a heat exchanger, typically referred to as a steam generator, in which the heat is transferred to a utilization circuit, such as a steam cycle driving turbine-generator apparatus, which produces electricity. The cooled water is then recirculated. The steam can be used in the acetylene reaction. The electricity can be used in the variety of reactions described heretofore. The gas-cooled nuclear reactor would provide more easily obtainable energy since gas exit temperatures are well over 700° C.

Ketene is a useful material that can be made to undergo a variety of reactions to produce high carbon chain hydrocarbons. Ketene can be used to form methylene. The methylene can be reacted with methane by an insertion chain reaction technique, to provide hydrocarbons such as heptane and octane; the methylene can be reacted with ketene to provide ethylene, ethane, acetylene and/or propane; the methylene can be reacted with acetylene to provide cyclopropene and allene; and the methylene can be reacted with ethylene to provide cyclopropane and propylene. The most valuable of these reactions is the insertion chain reaction.

Once ketene has been produced, $CH_2$ (methylene or carbene) can be easily formed by photochemical decomposition in the 2,400 to 3,800 Angstrom unit region, using, for example, an ultraviolet light source, or by solar energy, or by thermal energy, which again can use the nuclear power plant as a source. This decomposition proceeds according to the chemical reaction:

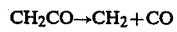

The methylene 24 produced may exist in two different spin states: one is where unshared electrons are paired, i.e., "singlet" methylene:

and the other is where the unshared electrons are not paired, i.e., "triplet" methylene

The triplet methylene is in fact a free diradical. The singlet form is the less stable and is the form usually first generated. The exact chemical properties of the methylene are affected by the reaction conditions used to produce it. Further details of this reaction and the methylene product can be found in Morrison and Boyd, *Organic Chemistry*, Boston, 1966, Ch. 4.33.

The decomposition means 25 can take the form of a pyrex glass tube, with a solar radiation source or a bank of suitable ultraviolet lamps, or a steel tube heated to a temperature of preferably between about 40° C. and about 75° C.

The carbon monoxide by-product of decomposition can remain with the methylene, without harming subsequent reactions. In the insertion means 26, preferably a long steel tube, methylene would be fed through line 27 at a flow rate of about 450 to 1,000 liters/hour for insertion reactor tube diameters of about 125 mm. The tube length could vary between about 15 to 30 meters, with a plurality of downstream methylene inlets about every 2 meters of length. The insertion reactor means could operate at 25° C. if methylene is converted from liquid ketene in a separate low temperature step, as described above. At the first methylene inlet 28, the following chemical reaction would occur to produce ethane:

$$CH_3H + CH_2 \rightarrow CH_3CH_3$$

The ethane formed would then be contacted with methylene from the adjacent spaced apart downstream inlet 29, and the following chemical reaction would occur to produce propane:

$$CH_3CH_2H + CH_2 \rightarrow CH_3CH_2CH_3$$

In this manner, butane, pentane, hexane, heptane and possibly octane would be formed. Thus, a methylene-alkane insertion chain reaction would be produced, to provide a high carbon chain hydrocarbon gas and/or liquid mixture 30.

Figure 3:
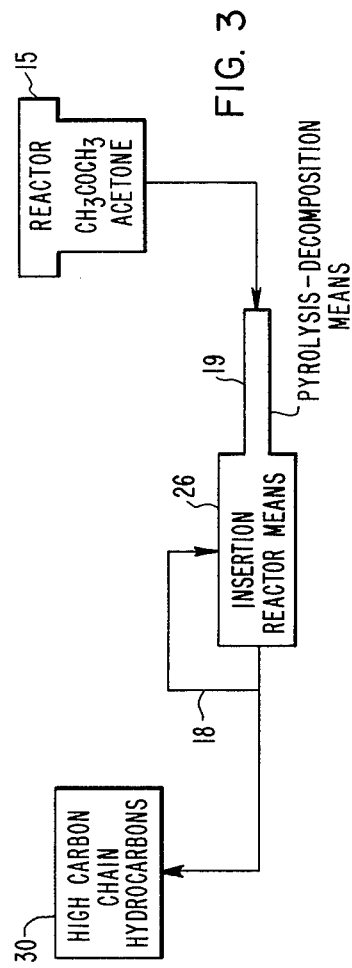
FIG. 3 is a flow chart of another embodiment of the method of this invention where pyrolysis and decomposition means are combined.

Gasoline is a mixture of hydrocarbons comprising heptanes, octanes, etc.; thus, by this process, inexpensive and plentiful carbonate type materials can be reacted to form gasoline-type molecules via a ketene reaction sequence and utilizing existing nuclear energy. It is also possible to combine the pyrolysis means and the decomposition means, and pyrolyze acetone and decompose the ketene product in a single stainless steel tube, maintained at about 600° C. to about 800° C., feeding directly into insertion reactor means. In this embodiment, the methane and carbon monoxide by-products formed would directly feed into the insertion reactor means with the methylene, as shown in FIG. 3 of the Drawings. While this would save ketene condensation, the methane would not be reacted with methylene in sequence, as shown in FIG. 1, and so longer chain hydrocarbons such as octane might not be formed. This could be alleviated by recycling a major portion of the formed hydrocarbons via line 18 back into the insertion reactor means where they could further react with methylene.

Other reactions of methylene, that can be used to produce hydrocarbons, include reactions with ketene as follows, to form ethylene, ethane, acetylene and/or propane:

$$CH_2CO + CH_2 \rightarrow CH_2=CH_2 + CO$$

$$CH_2CO + CH_2 \rightarrow CH_3 + CHCO$$

$$2CH_3 \rightarrow C_2H_6$$

$$2CHCO \rightarrow CH\equiv CH + 2CO$$

$$C_2H_4 + CH_2 \rightarrow C_3H_6$$

Methylene readily adds cross carbon-carbon double bonds. The simplest reaction involves the addition of methylene to ethylene to form cyclopropane and propylene:

$$CH_2=CH_2 + CH_2 \longrightarrow$$

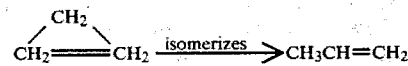

Alternatively, acetylene can be reacted with methylene to form cyclopropene and allene, according to the chemical reaction:

$$CH\equiv CH + CH_2 \longrightarrow$$

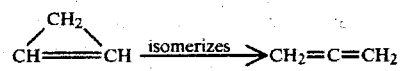

It is to be understood, that while $CaCO_3$ is the preferred carbon containing mineral feed, and the reactions have been described particularly relating thereto, the other carbonate containing materials set forth hereinabove would provide equally outstanding end results.

We claim:

1. A process of converting inorganic carbonate mineral material to organic hydrocarbon material, comprising the steps of:
   (1) thermally decomposing inorganic carbon containing carbonate mineral material at a temperature over about 700° C., to produce a product mixture comprising CaO and $CO_2$,
   (2) feeding the $CO_2$ produced in step (1) as a fuel into an electrolysis cell comprising an anode, a cathode, and an electrolyte therebetween, where $CO_2$ at the cathode is converted into CO and $O^=$,
   (3) catalytically decomposing the CO produced in step (2) at a temperature over about 450° C. to produce carbon particles,
   (4) reacting the carbon particles produced in step (3) from $CO_2$, with the CaO produced in step (1) at a temperature over about 1,600° C., to produce $CaC_2$ and CO, and then
   (5) water hydrolyzing the $CaC_2$ produced in step (4) to produce $C_2H_2$ and heat energy which is removed, and then
   (6) reacting the $C_2H_2$ produced in step (5) with excess steam in the presence of a catalyst effective to produce $CH_3COCH_3$, and then
   (7) high temperature pyrolyzing the $CH_3COCH_3$ produced in step (6) to produce ketene and methane,
   (8) where all the reactants except water and steam are derived from the carbonate starting material.

2. The method of claim 1, where the CO produced in step (4), is recycled to step (3) to be added to the CO from the electrolysis cell.

3. The method of claim 1, where the heat energy required for the electrolysis in step (2) and the pyrolyzing in step (7), is supplied, at least in part, by a nuclear reactor.

4. The method of claim 1, where the carbon produced in step (3) is a free-flowing, lamp black type carbon, the catalyst used in step (3) is selected from the group consisting of iron and stainless steel, and the catalyst used in step (6) is selected from the group consisting of catalyst containing zinc oxide, catalyst containing zinc vanadate, and mixtures thereof.

5. The method of claim 1, where after step (8), the ketene from step (8) is decomposed to provide methylene.

6. A process of converting inorganic carbonate mineral material to organic high carbon chain hydrocarbon material, utilizing nuclear reactor energy, comprising the steps of:
   (1) thermally decomposing inorganic carbon containing carbonate mineral material at a temperature over about 700° C., to produce a product mixture comprising CaO and $CO_2$,
   (2) feeding the $CO_2$ produced in step (1) as a fuel in a high temperature electrolysis cell comprising an anode, a cathode, and a solid electrolyte therebetween capable of allowing migration of $O^=$ ions therethrough from the cathode to the anode, where $CO_2$ at the cathode is converted into CO and $O^=$,
   (3) catalytically decomposing the CO produced in step (2) at a temperature over about 450° C., to produce carbon particles,
   (4) reacting the carbon particles produced in step (3) from $CO_2$, with the CaO produced in step (1) at a temperature over about 1,600° C., to produce $CaC_2$ and CO, and then
   (5) water hydrolyzing the $CaC_2$ produced in step (4) to produce $C_2H_2$ and heat energy which is removed, and then
   (6) reacting the $C_2H_2$ produced in step (5) with excess steam, at between about 250° C. and about 475° C., in the presence of a catalyst effective to provide gases which upon condensation yield $CH_3COCH_3$, and then
   (7) high temperature pyrolyzing the $CH_3COCH_3$ produced in step (6), at between about 600° C. and about 800° C., to produce ketene and methane,
   (8) decomposing the ketene from step (7) to produce methylene, and
   (9) reacting the methylene produced in step (8) with methane produced in step (7), to provide a product which is reacted with additional methylene in a manner effective to cause methylene insertion chain reactions and provide hydrocarbon materials containing at least three carbon atoms; where all the reactants except water and steam are derived from the carbonate starting material, and the heat energy required for the electrolysis in step (2) and the pyrolyzing in step (7) is supplied, at least in part, by a nuclear reactor.

7. The method of claim 6, where the carbonate mineral material is selected from the group consisting of calcite, dolomite, siderite, magnesite, rhodochrosite, smithsonite, arajonite, witherite, strontianite, cerussite, malachite, azurite, and mixtures thereof.

8. The method of claim 6, where the CO produced in step (4) is recycled to step (3) to be added to the CO from the electrolysis cell.

9. The method of claim 6, where the carbon produced in step (3) is a free-flowing, lamp black type carbon, the catalyst used in step (3) is selected from the group consisting of iron and stainless steel, and the catalyst used in step (6) is selected from the group consisting of catalyst containing zinc oxide, catalyst containing zinc vanadate, and mixtures thereof, and the carbonate material is limestone.

10. The method of claim 6, where ketene is separated from methane after step (7) by condensing ketene at about −60° C., after which it is allowed to vaporize.

11. The method of claim 10, where the ketene is in vapor form, and is decomposed in step (8) by heat and/or light energy.

12. The method of claim 6, where the methane reacts with methylene to form ethane, the ethane reacts with methylene to form propane, and the propane reacts with methylene to form butane; said methane being fed into a long tube reactor having a plurality of spaced apart downstream methylene inlets.

13. The method of claim 6, where the $CO_2$ from step (1) is bubbled through water before entering the electrolysis cell in step (2).

14. The method of claim 6, where the nuclear reactor utilized is liquid-cooled nuclear reactor.

15. The method of claim 8, where the heat energy required for the catalytic decomposition of step (3) and the reaction of carbon with CaO in step (4) are supplied at least in part by a nuclear reactor.

16. The method of claim 6, consisting of the steps of (1) through (10).

* * * * *